United States Patent
Kazatchkov et al.

(10) Patent No.: US 6,595,743 B1
(45) Date of Patent: Jul. 22, 2003

(54) HYDRAULIC SEAL FOR ROTARY PUMPS

(75) Inventors: Lev Kazatchkov, Mendoza (AR); Lucas Varela, Mendoza (AR)

(73) Assignee: IMPSA International Inc., Pittsburgh, PA (US)

(*) Notice: Subject to any disclaimer, the term of this patent is extended or adjusted under 35 U.S.C. 154(b) by 0 days.

(21) Appl. No.: 09/599,911

(22) Filed: Jun. 23, 2000

Related U.S. Application Data (63) Continuation-in-part of application No. 09/361,108, filed on Jul. 26, 1999, now Pat. No. 6,247,892.

(51) Int. Cl.[7] .............................................. F04D 29/08
(52) U.S. Cl. .................................. 415/171.1; 415/170.1
(58) Field of Search ......................... 415/170.1, 171.1, 415/173.1, 173.6

(56) References Cited

U.S. PATENT DOCUMENTS

| | | |
|---|---|---|
| 1,071,042 A | 8/1913 | Fuller |
| 2,470,794 A | 5/1949 | Snyder |
| 2,816,509 A | 12/1957 | Rice |
| 3,083,893 A | 4/1963 | Dean |
| 3,276,382 A | 10/1966 | Richter |
| 3,395,643 A | 8/1968 | Whitmore |
| 3,881,840 A * | 5/1975 | Bunjes ................. 415/171.1 |
| 4,779,614 A | 10/1988 | Moise |
| 4,846,152 A | 7/1989 | Wampler et al. |
| 4,908,012 A | 3/1990 | Moise et al. |
| 5,040,944 A | 8/1991 | Cook |
| 5,088,889 A * | 2/1992 | Wolff ................... 415/171.1 |
| 5,106,262 A * | 4/1992 | Oklejas et al. .......... 415/171.1 |
| 5,112,292 A | 5/1992 | Hwang |
| 5,209,650 A | 5/1993 | Lemieux |
| 5,232,338 A * | 8/1993 | Vincent de Paul et al. ...... 415/173.6 |
| 5,385,581 A | 1/1995 | Bramm et al. |
| 5,527,159 A | 6/1996 | Bozeman, Jr. et al. |
| 5,588,812 A | 12/1996 | Taylor et al. |
| 5,678,306 A | 10/1997 | Bozeman, Jr. et al. |
| 5,692,882 A | 12/1997 | Bozeman, Jr. et al. |
| 5,707,218 A | 1/1998 | Maher et al. |
| 5,890,883 A | 4/1999 | Golding et al. |
| 6,068,588 A | 5/2000 | Goldowsky |
| 6,247,892 B1 * | 6/2001 | Kazatchkov et al. .......... 415/68 |

* cited by examiner

Primary Examiner—John Kwon
(74) Attorney, Agent, or Firm—Fulbright & Jaworski L.L.P.

(57) ABSTRACT

A rotary blood pump comprising at least one rotor, a housing and at least one conduit in the rotor for conducting a by-passed portion of the blood into a clearance between the rotor and the housing, the portion of blood consisting mostly of plasma without red cells, thus preserving the solid particles and red cells from damage.

6 Claims, 6 Drawing Sheets

HYDRAULIC SEAL FOR ROTARY PUMPS

This patent application is a continuation-in-part application of U.S. application Ser. No. 09/361,108, filed Jul. 26, 1999, now U.S. Pat. No. 6,247,892.

BACKGROUND OF THE INVENTION

1. Field of the Invention

The present invention relates to rotary pumps, preferably rotary axial pumps with hydrodynamic bearing, for impelling a liquid through at least one stage with minimum friction and minimum or no shear forces transmitted to the fluid, and more preferably the invention relates to a hydraulic bearing and a continuous axial-flow rotary pump for use in pumping fluids having particles or components the integrity of which must be protected, such as for blood circulation assistance, either in intravascular or extravascular circuits, with no, or at least extremely minimized, damage in the red cells and platelets, and no, or extremely minimized, thrombus formation.

While particular reference will be made in the present specification to a blood pump, it should be understood that the present pump is for use in any other field wherein any fluid must be transferred or conveyed from one place to another one, either in a closed circulation system or in any open circuit or path, the fluid being preferably a fluid where care of its integrity must be taken.

2. Description of the Prior Art

It is well known to provide an axial-flow rotary pump comprising a generically cylindrical casing and/or stator with a rotor, or a plurality of rotors mounted inside the stator to drive a fluid through the pump. The driving of the liquid to transfer the same from an inlet of the pump to a pump outlet is based in the provision of energy to the liquid to increase the fluid pressure thereof. This energy, however, provides several undesired side effects. The elimination of these effects without impairing the pumping efficiency of the pump has been the aim of many developments in the field of pumps, particularly when handling of sensitive fluids, such as explosives, blood, etc., is involved.

Contours, sizes, assemblies and relative positions of the different parts, as well as the stationary and movable surfaces of a pump are aspects and parameters that must be defined when designing the pump. The final objective of the design is to get a maximum efficiency of the pump with a minimum or no side effects resulting from the energy transferred to the fluid during the impelling thereof. Particularly in the case of a blood pump design, the aim is to reach to a pump having a maximum efficiency without side effects causing blood damage and/or blood clotting during operation. Another important objective is to have a pump having a minimum size.

The side effects resulting from the energy transferred during rotation of the pump comprise the generation of secondary or side flows, vortex, cavitation and separation of the flow from the surfaces of the stationary and movable parts of the pump.

Figure 1:
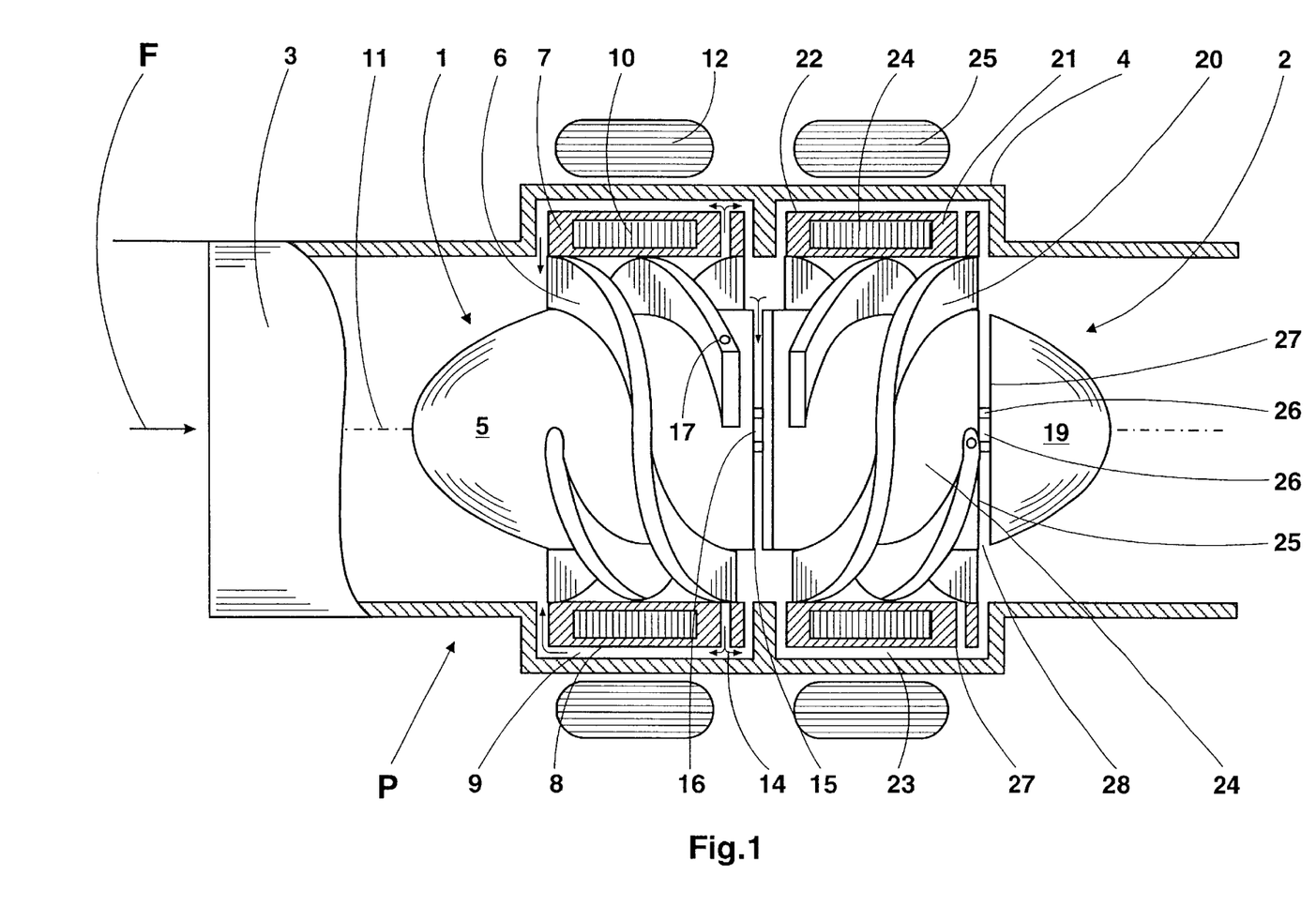
FIG. 1 shows a partially cross-sectional view of a blood pump according to a first embodiment of the present invention.

The continuous fluid flow behavior through a rotary pump provided with blades is mathematically defined by the Euler equation. According to Euler, pressure energy imparted by the rotor is proportional to the increment of the tangential component of velocity. Analysis of the Euler equation is made through the so called velocity triangles shown in FIG. 1 for a conventional scheme. Vectors represent averaged velocities on a flow surface and the letter references used in FIG. 1 are:

| | |
|---|---|
| ω | angular speed |
| R | radius |
| u = ω · R | rotation velocity |
| C | absolute velocity |
| W | relative velocity |
| $C_u$ | tangential component of absolute velocity | index 1 is used for the pump inlet
index 2 is used for the pump outlet
The Euler equation applied to a conventional rotary pump is:

$$(R \cdot C_u)_2 - (R \cdot C_u)_1 = \frac{g \cdot H}{\eta \cdot \omega}$$

where,
H Head
G Acceleration due to gravity
η Efficiency
if $C_{u1}=0$, we have $$C_{u2} = \frac{g \cdot H}{R_2 \cdot \eta \cdot \omega}$$

This is the reason why traditional pump designs include stator blades at the pump outlet, thus trying to reduce as much as possible the tangential component of the velocity and transform the kinetic energy into pressure energy.

Although many efforts have been made to eliminate or at least reduce the above mentioned side effects, by reducing or eliminating the above tangential component, for example, no solutions have been found hereinbefore. When a small Reynold's number is involved, that is when one handles small pumps and/or viscous liquids, stator blades at the pump outlet can not effectively reduce the tangential component of the velocity and transform kinetic energy into pressure energy, no matter the shape or number of blades provided. Therefore, flow separation and side flows are formed at the stator blades which cause hemolysis and blood clotting.

It is also well known to provide an axial-flow rotary pump comprising a generically cylindrical casing or stator with a rotor, or a plurality of rotors mounted inside the stator to drive a fluid, such as a liquid, through the pump. The driving of the liquid to transfer the same from an inlet of the pump to a pump outlet is based in the provision of kinetic energy to the liquid to increase the pressure thereof. This kinetic energy, however, while providing the impelling of the fluid it also provides several undesired side effects. The elimination of these effects without impairing the pumping efficiency of the pump has been the aim of the many developments in the field of pumps, particularly when the handling of sensitive fluids, such as explosives, blood, etc., is involved.

Regarding blood pumps, it is known that the rotary pumps for pumping blood, particularly those to be implanted in the human body, for circulatory assistance, causes severe damages in the blood, i.e. hemolysis. The higher or lesser extent at which the blood is damaged will depend on many factors, one the main factors being the high shear forces or stresses affecting the red cells and platelets, such stresses appearing in zones between pump components with relative movements and close to each other or, worst, in contact with each other.

Figure 3:
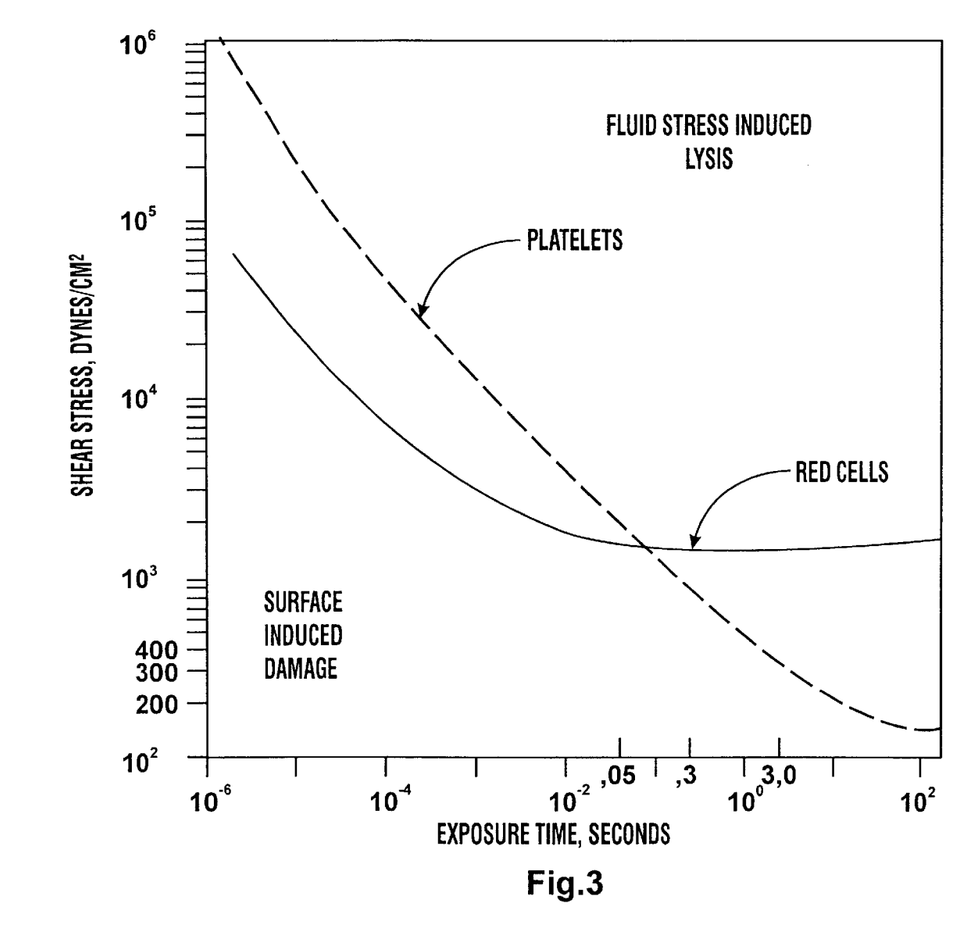
FIG. 3 is a X–Y chart showing tolerances to shear stress and exposure time of platelets and red cells.

According to Publication No. 85-2185; 1985; from the National Institute of Health (NIH), entitled "Guidelines for Blood-Material Interactions", it is generally accepted that the quantity of red cells and platelets damaged by shear stresses depends on the intensity or magnitude of the stresses and the period of time the red cell and/or platelet is exposed to the stresses for a determined quantity of hematocrit. The hematocrit is the volume percentage of red cells in the blood. FIG. 3 shows experimental results of blood damage, illustrated in curves corresponding to the tolerance of blood to shear forces, with the shear stresses shown in the Y-axis and the exposure time shown in the X-axis. The region above the curves corresponds to a significant particle destruction. It is shown that the shear stress that can be tolerated by the red cells is below 10 dynes/cm2. There are some regions in the rotary blood pumps, such as in the hydrodynamic bearing housings and in the gap or clearance between the peripheral edge of the pump blades and the inner surface of the stationary casing, housing or stator, wherein the shear forces and stresses generated by the relative movement between the rotor and the casing surfaces exceed the above mentioned tolerated stress value.

The hydrodynamic bearings have shown a good behavior to support mechanical components in relative movement because of the fluid pressure increase in the bearing cavity. This effect requires an important circulating flow to guarantee a continuous operation of the pump and high shear stresses are involved due to the relative speed of the pump components. In gap between the periphery of the blades and the inner surface of the casing a high pressure drop is generated because the high pressure side of the blade and the low pressure side of the blade are joined at this periphery. In addition, like in the hydrodynamic bearings, the shear stresses are high due to the flow speed gradients in the area.

Blood is a tissue composed of plasma and several types of suspended particles having different densities. The plasma is the liquid portion of the blood and is constituted by about 90% of water. While the plasma is not affected, or affected in a lesser extent, by the above mentioned shear forces the particles such as the red cells may be destroyed by such forces and stresses.

Although many efforts have been made to solve or at least reduce the above mentioned problems of the rotary pumps, particularly rotary blood pumps, there is still a need for a blood rotary pump with means for reducing or eliminating the prejudicial shear forces and stresses particularly appearing in the clearances between the rotor and stator or casing, which shear forces are the cause of important damages in the blood integrity.

The following patents describe attempts made to solve the above mentioned drawbacks associated with rotary pumps, more particularly with rotary blood pumps.

U.S. Pat. No. 4,908,012 to John C. Moise, discloses an implantable ventricular assistance pump having tube in which a pump rotor and stator are coaxially contained, and purge fluid is introduced into stator blades of the pump to avoid creation of discontinuities in the blood path wall. The object of this cited patent is reduce the size of the implant and minimize the risk of infection by reducing vibration, minimizing the percutaneous conduit, and directing most of the heat generated by the pump into the blood. No mention to the problem of shear stresses are found neither solved by the patent. Also, the problem of the flow kinetic energy is not addressed and, in fact, the provision of the bladed stator does not reduce the tangential component of the flow speed.

U.S. Pat. No. 5,209,650 to Guy B. Lemieux, discloses a pump integral with an electric motor and impeller assembly that rotates within a stator casing and is supported on hydrostatic radial and thrust bearings so as to avoid having to provide external seals or friction type bearings. As it is clearly disclosed in its specification, the invention addresses the problems that occur with leaking mechanical seals and worn bearings. The problem of shear forces and stresses is not addressed. While Lemieux specifically includes stay vanes pitched to diffuse the liquid from the second stage integral rotor and impeller assembly, the problem of kinetic energy and tangential components of the blood flow is not considered, and it can not be overcome in any way by providing, as disclosed and illustrated in this patent, axial rotors separated by axial stators.

U.S. Pat. No. 5,678,306 to Richard J. Bozeman discloses a method for reducing the damages to the blood by optimizing each of a plurality of blood pump configuration parameters in the known pump components and variations. The process comprising selecting a plurality of pumps components believed to affect blood damage, such as the clearance between the blades and housing, number of impeller blades, rounded or flat blade edges, variations in entrance angles of blades, impeller length and the like. Construction variations are selected for each of the components and these variations are listed in a matrix for comparison of results. Each variation is tested and the total blood damage is determined for the blood pump and, finally, the least hemolytic variation for each pump component is selected as an optimized component. While considerations are made related to the blood damage and the clearance between the housing and the blades, the problem is attempted to be solved by modifying the clearance size and blade-housing geometry without providing any means to seal the clearance at the peripheral edge of the blades.

U.S. Pat. No. 5,055,005 to Kletschka, discloses a fluid pump with an electromagnetically driven rotary impeller levitated by localized opposed fluid forces which levitation eliminates the need for bearings and seals in the driving mechanism. The shear stresses appearing at the levitating areas are dramatically high which causes the blood to be damaged. No considerations are made in connection to means for preventing the blood from damaging under these circumstances.

U.S. Pat. No. 4,382,199 to Issacson discloses a hydrodynamic bearing for a motor driving a pump for an artificial heart. The motor stator has a bore and a rotor with its impeller is slidable and rotatable in the bore. Both rotor and impeller are supported hydrodynamically such that the tendency is for the entire rotor/impeller assembly to be completely suspended by fluid. It is well apparent that high shear stresses will appear between the rotor assembly and the motor stator without effective means being provided to solve this problem.

U.S. Pat. No. 5,049,134 to Golding et al, discloses a blood pump with two hydrodynamic bearings located at the ends of the rotating impeller. The bearings include helical screws for urging the blood through the pump with lubricating and cooling purposes. In addition, the rotatable impeller includes a bore permitting a continuous blood flow from the blades towards the hydrodynamic bearings. The shear stresses in the hydrodynamic bearings are high enough to damage the blood and no solution is provided to this problem.

Other references, such as U.S. Pat. Nos. 3.083.893 to Dean; 3.276.382 to Richter; 2.470.794 to Snyder and 1.071.042 to Fuller provide two or more rotor pumps but they do not address the problem of handling blood and, sealing the gap between the rotors and the casing.

It would be therefore convenient to have a rotary pump, preferably a rotary blood pump, having a minimum quantity of components and capable of providing a continuous flow with minimized, or without, stresses, particularly shear stresses or forces that would damage the circulating fluid, affecting the fluid integrity, particularly blood in a rotary blood pump.

SUMMARY OF THE INVENTION

It is therefore one object of the present invention to provide a rotary pump for impelling a fluid, preferably a fluid that must be preserved of any damage, more preferably blood, wherein the rotary pump comprises at least one rotor, a housing and means for forming a seal and/or a bearing at a clearance or gap between the rotor and the housing.

It is a further object of the invention to provide a blood pump with sealing means comprising the provision of a by-passed portion of blood to the clearance between the rotor and the housing, the portion of blood consisting mostly of plasma without red cells, thus preserving the solid particles and red cells from damage.

It is still another object of the present invention to provide a rotary blood pump comprising at least one rotor, a housing or casing and means for by-passing a portion of the blood under pumping into a clearance between the rotor and the casing with the purpose of forming a seal and/or bearing, the portion of blood being taken at a location of the pump where the blood, as a result of centrifugal forces appearing in the blood mass due to the rotation of the rotor, is composed mostly of plasma and other particles, practically without red cells. Therefore, the by-passed portion of the blood, used for sealing and/or bearing purposes, has no red cells which, otherwise would be affected by the shear forces appearing at the clearance between the rotor and housing.

It is also a further object of the present invention to provide a hydrodynamic sealing means for a rotary pump, the pump being of the type comprising at least one rotor arranged within a stationary casing, the rotor comprising a hub and at least one fluid impelling blade in the hub, a gap being defined between a periphery of the rotor and the casing, the sealing means comprising at least one conduit in the rotor for conducting a by-passed portion of the fluid under pumping, the conduit having an outlet located at the periphery of the rotor and an inlet located radially inwardly relative to the outlet, wherein the by-passed portion of fluid enters the inlet of the conduit and exits the outlet of the conduit into the gap to form a pressurized fluid seal between the rotor and the casing.

It is even another object of the present invention to provide a rotary pump for driving fluid, preferably a blood pump, the pump comprising a stationary casing, at least one rotor rotatably mounted in the casing, the rotor comprising a hub and at least one impelling blade in the hub, for impelling the fluid, a gap between a periphery of the rotor and the stationary casing, and at least one conduit in the rotor for conducting a by-passed portion of the fluid under pumping, the conduit having an outlet located at the periphery of the rotor and an inlet located radially inwardly relative to the outlet, wherein the by-passed portion of fluid enters the inlet of the conduit and exits the outlet of the conduit into the gap to form a pressurized fluid seal between the rotor and the casing.

It is a further object of the present invention to provide a continuous axial-flow pump for impelling a fluid under a continuous pattern without side effects to minimize and eliminate damage to fluid, the pump having at least one stage, comprising an outer casing and rotor means mounted in the casing, the rotor means comprising at least two adjacent rotors rotating in opposite directions.

The above and other objects, features and advantages of this invention will be better understood when taken in connection with the accompanying drawings and description.

BRIEF DESCRIPTION OF THE DRAWINGS

The present invention is illustrated by way of example in the following drawings wherein.

DESCRIPTION OF THE PREFERRED EMBODIMENTS

Figure 2:
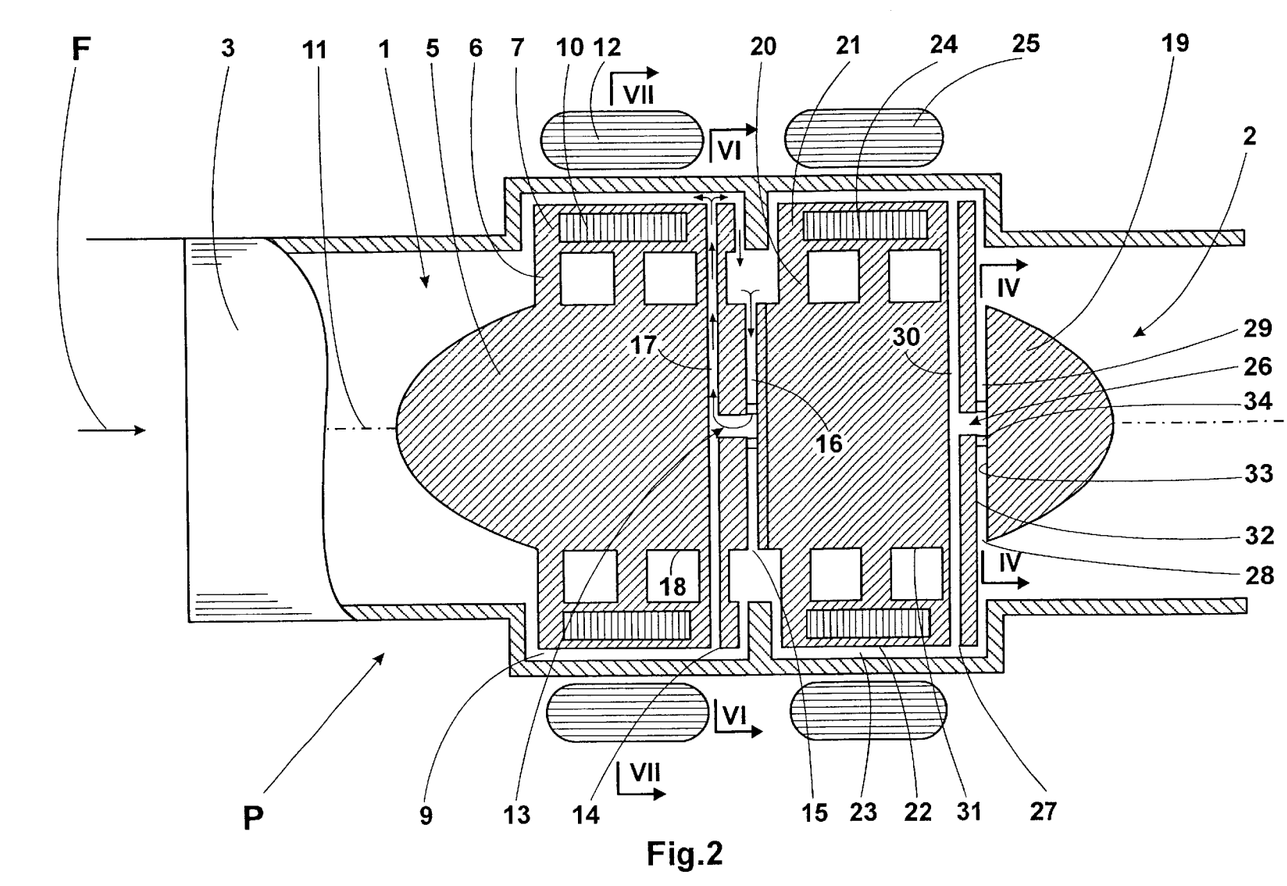
FIG. 2 shows an entirely cross-sectional view of the blood pump of FIG. 1.

Now referring in detail to the drawings it may be seen from FIGS. 1 and 2, that a preferred embodiment of the invention comprises a rotary pump, preferably a rotary blood pump, indicated by the general reference P.

Considering that the flow direction and sense is from the left to right as indicated by arrow F, the pump preferably comprises an upstream rotor 1 and an adjacent downstream rotor 2 rotatable in opposite directions within a housing stator or casing 3 forming a recess 4. Rotor 1 comprises a hub 5 with impelling blades 6, at least one blade or, preferably four helical blades 6. Rotor 1 includes a coaxial concentric band 7 having an inner surface joined to the periphery of blades 6 and a peripheral outer surface 8 facing an inner surface of the casing and slightly spaced apart from the casing to define a hydrodynamic clearance or gap 9. Band 7 includes permanent-type magnets 10 in order to cause rotor 1 to rotate within the casing, around axis 11, under the magnetic action of stator coil 12 that is coaxially wounded around axis 11 encircling band 7, or axisymetrical band, and magnets 10. While the pump according to the invention has preferably two adjacent rotors 1 and 2, the invention may be easily applied to a pump with only one rotor, rotor 1 for example.

Assuming that the pump has only one rotor, rotor 1, the blood is drawn from the left hand side of the Figure, is impelled by the blades and is conducted towards the right hand side of the Figure, along the casing. Due to the relative movement between the band that defines a periphery of the rotor and the casing, high shear forces or stresses appear in the clearance or gap 9, more precisely between peripheral surface 8 and the inner surface of casing 3. Under such shear forces the particles of the blood are seriously damaged and destroyed but the blood, however, is necessary in such clearance to give hydrodynamic support to the rotor. In other words, the rotor is completely suspended by the blood within the casing, with the blood, however, being subject to destructive shear forces in such suspension regions, i.e. clearance of the pump.

According to the invention, such desired support can be obtained from the blood without subjecting the integrity of same to destructive stresses. More particularly, a portion of the blood composed by plasma is separated from the blood flow and is by-passed to the clearance or gap for supporting and sealing purposes. Such by-passed portion of the blood is not affected by the shear forces as long as it has a low content of particles such as red cells. The red cells are highly sensitive to compressing and shear forces like the ones appearing in the clearance between the rotor and the casing.

According to the invention, means are provided to conduct such by-passed portion of blood to the clearance, the means comprising at least one conduit 13 in the rotor, the conduit having an outlet 14 located at the periphery of the rotor and an inlet 15 located radially inwardly relative to the outlet, wherein the by-passed portion of fluid enters inlet 15 and exits outlet 14 into gap 9 to form a pressurized fluid seal between the rotor and the casing. More particularly, the conduit comprises a first portion or first conduit 16 radially extended from inlet 15 towards a center of the rotor for conducting said by-passed portion of fluid towards the center of the rotor, and a second portion or second conduit 17 in fluid communication with the first conduit, radially extended from the center of the rotor to outlet 14, for conducting the portion of fluid from the center of the rotor to the outlet into the gap.

Since inlet 15 is radially inwardly located in the rotor relative the location of outlet 14, conduit 13 will operate like a centrifugal pump, for example. First conduit 16 will take blood adjacent to the peripheral surface of hub 5 and will conduct the by-passed portion of the blood to outlet 14 radially outwardly located, at the peripheral surface of band 7. Hub 5, blades 6 and band 7 are preferably an integral piece, and second conduit 17 extends through the hub, the blades and the band. The blood under pumping, more particularly in the region of the rotor, is subject to a rotational movement that causes the heavier particles of the blood to be outwardly radially expelled towards the periphery of the pump, namely towards the casing. As a result of this effect, the red cell are found radially outwardly spaced from the peripheral surface 18 of the hub with the plasma being adjacent to surface 18 of the hub. Since inlet 15 is at surface 18 of hub 5 most of the blood entering the inlet will be composed of plasma without red cells or with a very low content of red cells.

In addition to the foregoing effect, the means of the invention permits to separate the suspended particles of the blood, such as red cells that may be damaged by the shear stress. In the region of inlet 15 of conduit 16 the particles are separated from the plasma, because the walls of the conduit are under rotary movement. Under this movement, the blood particles are forced to follow a curve path contrary to the natural tendency of following a rectilinear course at constant speed. This imposes the particles an inertial force generated by the rotational movement, namely the centrifugal force, that prevents the particles heavier than the plasma from entering the conduit. Conduit 17, at an impeller region thereof, operates like a centrifugal pump by increasing the pressure as the radius of the conduit increases towards the outlet of the conduit at the clearance.

The sealing and/or bearing effect in the high shear stresses areas, namely the clearance between the blades and the casing, is achieved by conducting to the clearance the by-passed portion of blood with low content of particles. The seal is effective in separating the particles of the blood and conducting the fluid towards the areas of the pump with high shear stresses. For determined conduit diameters and determined rotation speeds of the rotor a defined and controlled quantity of plasma with low content of particles are conducted to the areas of the pump with high shear stresses.

In the preferred embodiment with two rotors 1 and 2, the invention operates in like manner as it will be described now. Rotor 2 comprises a hub 19 with impelling blades 20, at least one blade or preferably four helical blades 20. Rotor 2 includes an outer coaxial concentric band 21, or axisymetrical band, having an inner surface joined to the periphery of blades 20 and a peripheral outer surface 22 facing an inner surface of the casing and slightly spaced apart from the casing to define a hydrodynamic clearance or gap 23. Band 21 includes permanent-type magnets 24 in order to cause rotor 2 to rotate within the casing, around axis 11, under the magnetic action of stator coil 25 that is coaxially wounded around axis 11 encircling band 21 and magnets 24.

As discussed above, between the periphery of the rotor, defined by the outer peripheral surface 22 of band 21 high shear forces or stresses appear in the clearance or gap 23. To counteract this effect sealing means, like in rotor 1, is provided. This means comprises at least one conduit 26 in the rotor, the conduit having an outlet 27 located at the periphery of the rotor and an inlet 28 located radially inwardly relative to the outlet, wherein the by-passed portion of fluid enters inlet 28 at a peripheral surface 31 of hub 19 and exits outlet 27 into gap 23. More particularly, the conduit comprises a first portion or first conduit 29 radially extended from inlet 28 towards a center of the rotor and a second portion or second conduit 30 in fluid communication with the first conduit, radially extended from the center of the rotor to outlet 27.

Figure 4:
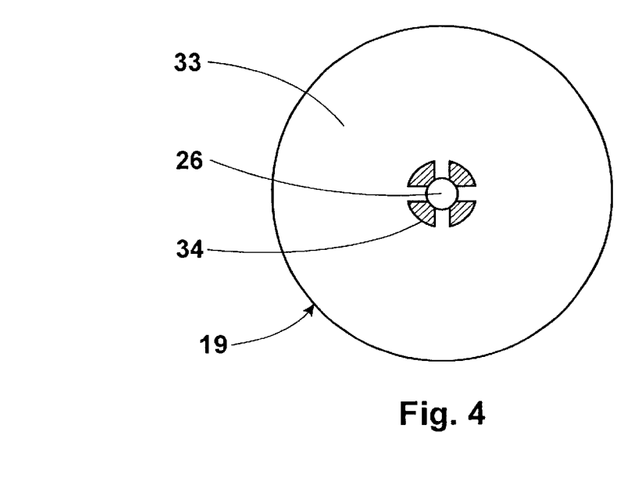
FIG. 4 shows a cross-sectional view taken along line IV—IV of FIG. 2.

FIG. 4 shows a cross-sectional view through first portion 29 of conduit 26, taken along line IV—IV of FIG. 2. As it may be seen from FIG. 4, first portion 29 is in fact a cylindrical passage formed between walls 32 and 33 of hub 19. A central portion 34 keeps the integrity of the parts of hub 19 that are separated by passage 29, and orifices 35 are provided in portion 34 to keep passages 29 and 30 in fluid communication. While the cut through line IV—IV has been taken along conduit 29 of rotor 2 for clarity purposes, the construction of conduit 16 of rotor 1 is the same, with a like cylindrical passage for conduit 16 and a central support with orifices.

Figure 6:
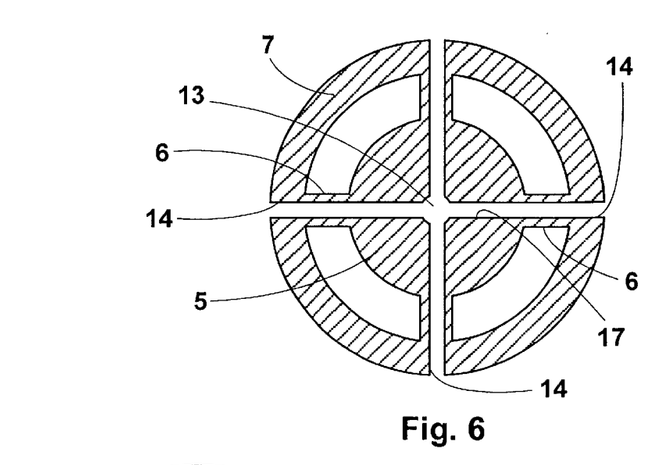
FIG. 6 shows a cross-sectional view taken along line VI—VI of FIG. 2.

FIG. 6 shows a cross-sectional view through second conduit 17 of conduit 13, taken along line VI—VI of FIG. 2. While the cut through line VI—VI has been taken along conduit 17 of rotor 1 for clarity purposes, the construction of conduit 30 of rotor 2 is the same.

Figures 5, 7:
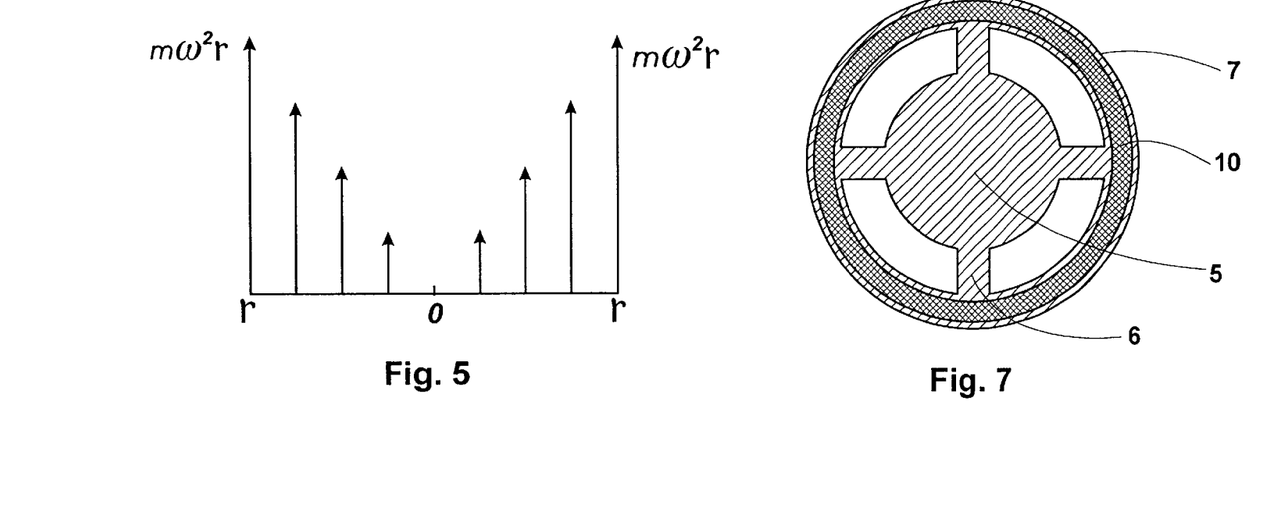
FIG. 5 is a chart showing the variation of the centrifugal forces according to the radius of the rotor in the hydrodynamic bearing.
FIG. 7 shows a cross-sectional view taken along line VII—VII of FIG. 2.

FIG. 7 shows a cross-sectional view through rotor 1, taken along line VII—VII of FIG. 2. While the cut through line VII—VII has been taken along rotor 1 for clarity purposes, the construction of rotor 2 is the same.

While conduits 13 and 26 of rotors 1, 2, with the first and second conduits 16, 17, 29, 30, have been shown in the downstream ends of rotors 1, 2, such conduit may be provided at any other location of the rotors as long as the inlets are radially inwardly located relative to the outlets of the conduits.

Next the centrifugal effect of the rotary movement on the blood and the portion of the blood that is by-passed through conduits 13, 26 will be explained. When an explanation is given in relation to one of the rotors, the same concepts apply to the other. When the rotor is under rotation, wall 33 rotates with an angular speed ω and the pressure in the conduit at the center of the rotor is lower than the pressure at the inlet of the conduit. Due to this pressure drop the blood enters 15, 28 wherein the blood particles are affected by a centrifugal force determined by the following equation:

$$F_{centr} = m\omega^2 r$$

wherein:

$F_{centr}$: centrifugal force.

m: particle mass.

ω: angular speed.

r: distance to longitudinal axis of rotor

Particles having a mass larger than the mass of plasma are affected by a larger centrifugal force. FIG. 5 shows that the centrifugal force has a maximum value at inlets 15, 28 of the conduits where the largest separation of particles occurs. Thus, the by-passed portion of blood reaches the center of the hub with a minimum content of particles. From the center of the hub, the blood portion flows outwardly through conduit portion 17, 30 with an energy that may be mathematically expressed by the Bernoulli equation, in relation to a coordinate system rotating with the rotor:

$$\frac{w_1^2}{2g} + \frac{p_1}{\gamma} - \frac{(r_1\omega)}{2g} = \frac{w_2^2}{2g} + \frac{p_2}{\gamma} - \frac{(r_2\omega)}{2g} + \Delta h \quad (1)$$

wherein:

w: relative speed in the conduit.

P: pressure.

ω: angular speed of rotor.

r: distance to longitudinal axis of rotor.

g: gravity force. Y: unitary weight. Δh: energy drops of the blood between the inlet and outlet Index 1 indicates inlet.

Index 2 indicates outlet.

Rearranging the terms of equation (1) the following is obtained:

$$\frac{p_2 - p_1}{2g} = \frac{w_1^2 - w_1^2}{2g} + \frac{\omega^2(r_2^2 - r_1^2)}{2g} - \Delta h \quad (2)$$

If the areas of inlet sections and outlet sections are the same, then the relative speed of the fluid in the conduit is constant; $W_1 = W_2$ The energy drops of the fluid between the inlet and the outlet are proportional to the flow circulating by the conduit, $$\Delta h = \xi \frac{Q^2}{2g}$$

WHEREIN:

Q: flow circulating in the conduit,

ε: resistance coefficient of the conduit, it depends on the conduit length, diameter and section area.

Replacing coefficient ε in formula (2):

$$\frac{p_2 - p_1}{2g} = \frac{\omega^2(r_2^2 - r_1^2)}{2g} - \xi\frac{Q^2}{2g} \quad (3)$$

Values P1, P2 and ε depends on flow conditions in the pump and the pumping rate of the pump. Values r1 and r2 are elected during the design of the pump. Flow Q circulating in the conduit is defined by equation (3). Q value is necessary for hydrodynamically sealing the gap or clearance of the bearing and such value may be determined by electing a proper combination of conduit shape, conduit length, size and diameter, according to equation (3).

While the inventive pump has been illustrated and described with sealing/bearing means and recess 4, the pump of the invention may comprise only two adjacent impellers or rotors 1, 2. Blades 6 are twisted in opposite or reversed direction relative to blades 20. Rotors 1, 2 rotate, according to the concepts of the invention, in opposite directions around longitudinal axis 11 of the pump. According to the rotary directions the left side of FIG. 1 corresponds to inlet F of the pump while the right side of the Figure corresponds to the outlet of the flow. Preferably, opposite outer ends of rotors 1, 2 are cone-shaped to accommodate the fluid flow. Inner facing ends of rotors 1, 2 are adjacent so that an outlet of rotor 1, when rotor 1 is an inlet rotor, is adjacent to an inlet of rotor 2 when rotor 2 defines an outlet rotor. The "inlet" and "outlet" terms are used to qualify the rotor that is at the inlet side or at the outlet side of the pump. Obviously, the inlet and outlet of the pump will depend on the rotary directions of the rotors.

Rotors 1, 2 may be conveniently arranged within a casing, preferably a cylindrical, tubular casing and stator motor components 12, 25 may be provided to drive the rotors. First rotor 1 rotates by the driving action of stator motor 12 and transfers energy to the fluid flow, preferably the blood flow, and increases the tangential component of velocity of the flow. Rotor 2 counter rotates under the action of stator motor component 25 and transfers pressure energy to the flow as well as eliminates the above cited tangential component at the outlet side of the pump for given combinations of heads and discharges or outputs. Blades 6, 20 are twisted around the rotors, more precisely, the blades extend helically over the rotors with blades 6 defining a first-direction helix and blades 20 defining a second-direction helix opposite to the first-direction.

Figure 8:
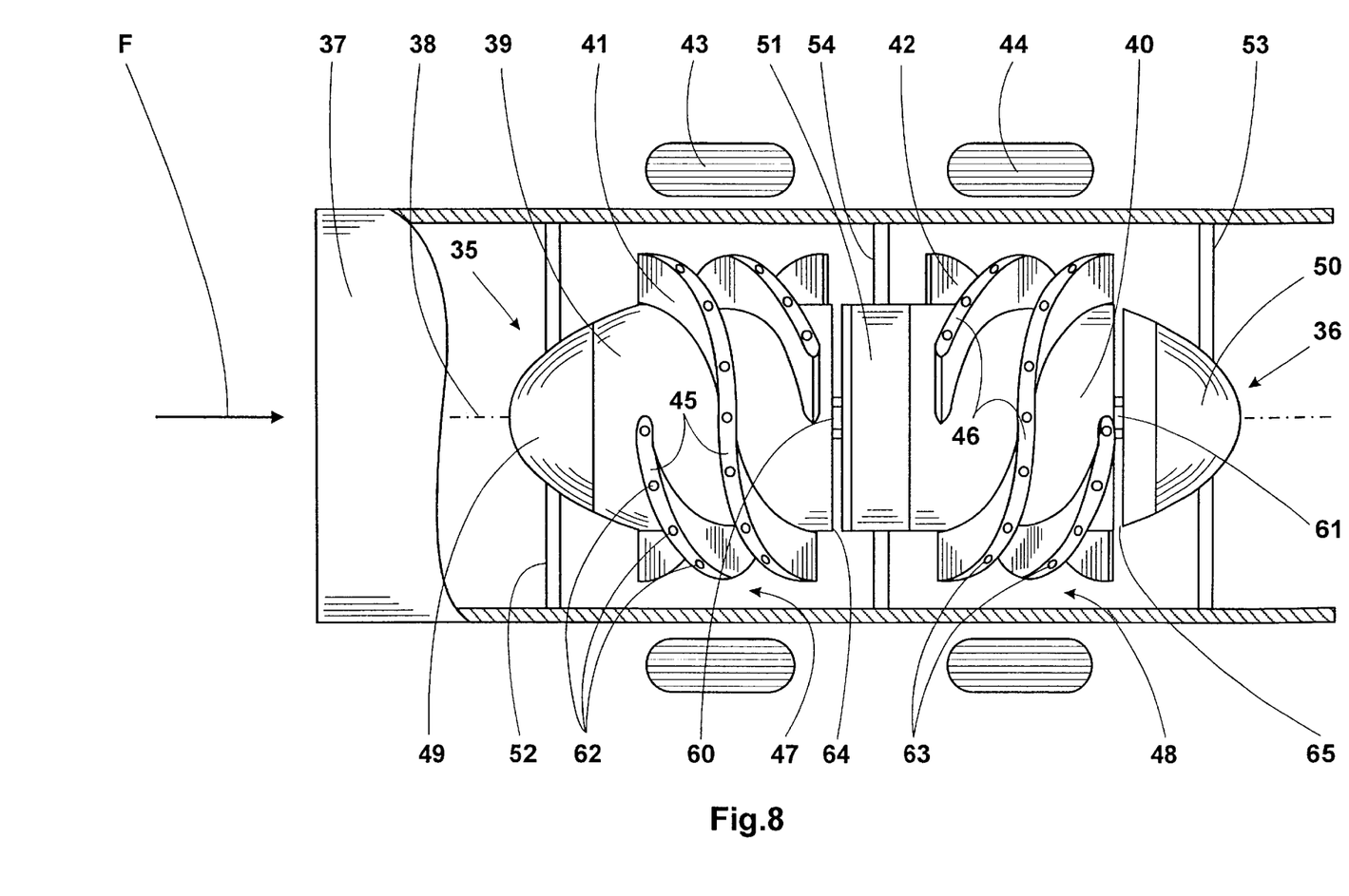
FIG. 8 shows a partially cross-sectional view of a blood pump according to a second embodiment of the present invention.
Figure 9:
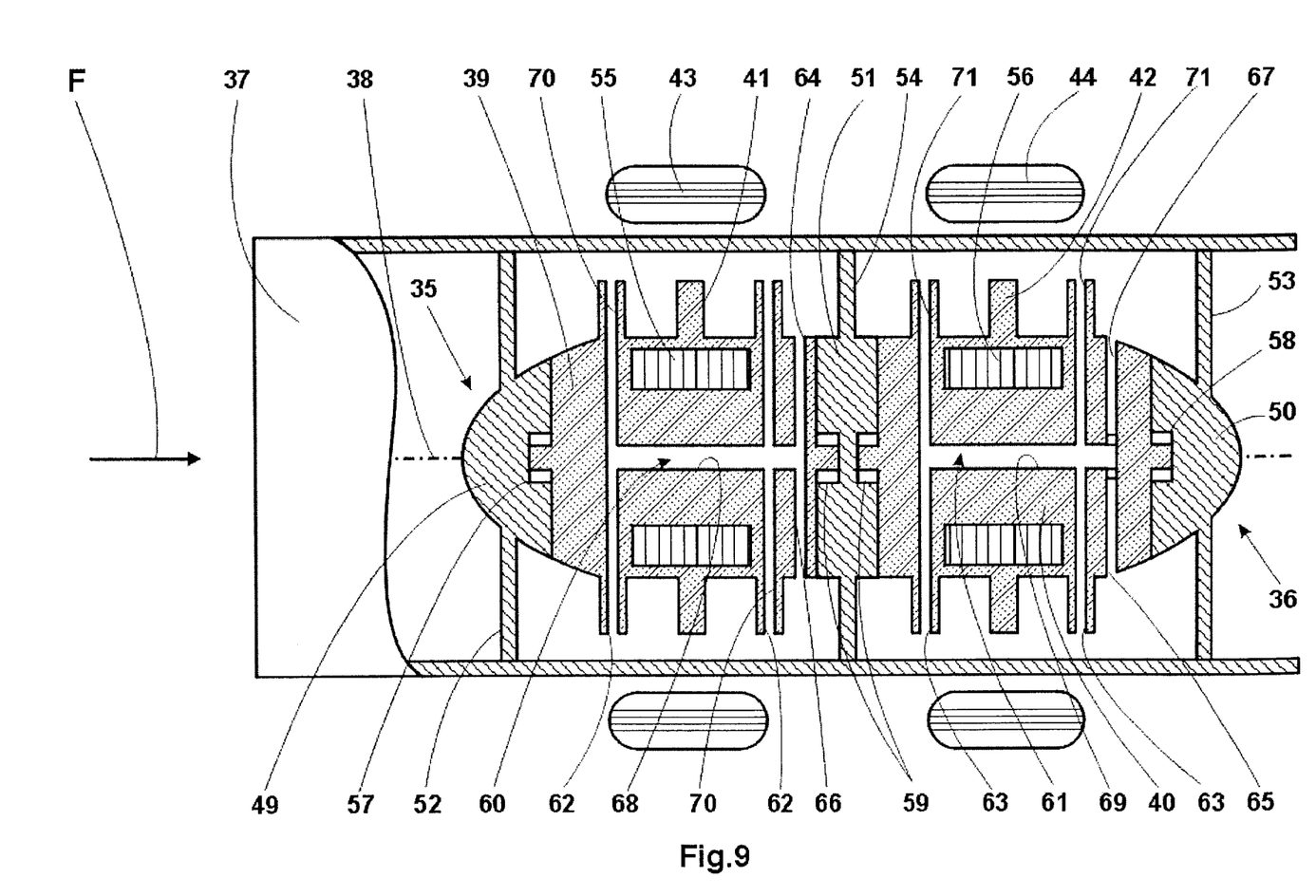
FIG. 9 shows an entirely cross-sectional view of the blood pump of FIG. 8.

According to another embodiment of the invention FIGS. 8, 9 show a rotary pump differing from the one above described, in that the casing of this second embodiment does not provide a recess for housing the rotor but the rotor is rotatably mounted inside the casing by mounting means.

With F being the flow direction and sense, the pump preferably comprises an upstream rotor 35 and an adjacent downstream rotor 36 rotatable in opposite directions within a tubular housing, stator or casing 37. Rotors 35, 36 may be connected by a shaft, not shown, in order to rotate around the same axis, with opposite directions and, if desired, at different speeds. Rotors 35, 36 respectively comprises a hub 39, 40 with at least one impeller blade 41, 42, each rotor having preferably four helical blades.

Hubs 39, 40 includes permanent magnets 55, 56, for causing the rotors to rotate under the electromagnetic field induced by the stator coils 43, 44.

The periphery of the rotors is defined by the outermost peripheral surface or peripheral edges 45, 46 of blades 41, 42, and a gap or clearance 47, 48 is defined respectively between edges 45, 46 and the inner surface of casing 37.

Rotors 35, 36 are mounted inside the casing by mounting means capable of holding both rotors onto the casing. The mounting means includes respective cone supports 49, 50 and a common central support 51, with supports 49, 50 and 51 being connected by respective vanes 52, 53 and 54 circumferentially spaced around the cone and central supports to the casing. The support means, i.e. cone support, central support and vanes are held securely onto the casing by any securing means, such threads, welding, etc. Hubs 39, 40 may be rotatably mounted on supports 49, 50, 51 by any suitable bearing means, such as ball bearings, needle bearings, etc. which have been diagrammatically shown and indicated by references 57, 58 and 59.

The sealing and/or bearing means according to the invention may be arranged in the rotors in a manner like in the above described first embodiment, except that no band concentric to the rotors are provided, but the blade edges 45, 46 are free of any covering structure and directly face the inner surface of the casing. Like in the first embodiment of the invention, the shear forces in the gaps 47, 48 are counteracted by supplying a portion of blood to the gaps. More particularly, a portion of the blood composed by plasma is separated from the blood flow and is by-passed to the clearance or gap for sealing purposes. Such by-passed portion of the blood is minimally affected by the shear forces as long as it has a low content of red cells.

According to the second embodiment of the invention, the means to conduct such by-passed portion of blood to the clearance, comprise at least one conduit 60, 61 respectively in each 35, 36 of the rotors. Each conduit 60, 61 has at least one outlet 62, 63 located at the periphery of the rotor, namely at the peripheral edge 45, 46 of blades 41, 42, and at least one inlet 64, 65 located radially inwardly relative to the outlet, at a peripheral surface of hub 39, 40. The by-passed portion of blood enters inlets 64, 65 and exits outlets 62, 63 into gap 47, 48, respectively, to form pressurized fluid seals between the blade peripheral edges and the casing. More preferably, each conduit comprises a first portion or first conduit 66, 67 radially extended from inlet 64, 65 towards a central conduit 68, 69, for conducting said by-passed portion of fluid towards the central conduit of the rotor, and at least one second portion or second conduit 70, 71 in fluid communication with the central conduit and radially extended from the center of the rotor to outlets 62, 63, for conducting the portion of fluid from the center of the rotor to the outlet into the gap 47, 48.

With basically the same effect like in the first embodiment blood enters inlets 64, 65 and, since these inlets are radially inwardly located in the rotor relative the location of outlets 62, 63, conduits 60, 61 will operate, for example, like a centrifugal pump by taken a portion of blood with a minimum content of red cells at inlets 64, 65, the blood will be conducted through conduits 66, 67, via central conduits 68, 69, and through conduits 70, 71 and outlets 62, 63 into gaps 47, 48.

Like in the embodiment of FIG. 1, the pump may comprise only one rotor with the teachings of the invention. More particularly, pump of FIGS. 8, 9 may comprise a rotor 35 with the sealing means 60, 62, 64 according to the invention, without rotor 36 but with support means 49, 51, 52, 54 provided at the locations they are shown in such Figures.

While preferred embodiments of the present invention have been illustrated and described, it will be obvious to those skilled in the art that various changes and modifications may be made therein without departing from the scope of the invention as defined in the appended claims.

We claim:

1. Hydrodynamic sealing means for a rotary pump, the pump being of the type comprising at least one rotor arranged within a stationary casing, the rotor comprising a hub and at least one fluid impelling blade in the hub, a gap being defined between a periphery of the rotor and the casing, the sealing means comprising:

at least one conduit in the rotor for conducting a by-passed portion of the fluid under pumping, the conduit having at least one outlet located at the periphery of the rotor communicating with the gap, and at least one inlet located radially inwardly relative to the outlet;

a first portion of the conduit radially extended from the inlet towards a center of the rotor for conducting said by-passed portion of fluid towards the center of the rotor;

a second portion of the conduit in fluid communication with the first conduit portion, radially extended from the center of the rotor to the conduit outlet, for conducting the portion of fluid from the center of the rotor to the outlet into the gap.

2. The sealing means of claim 1, wherein the rotor includes a coaxial outer band having an outer axisymetrical peripheral surface, the blade being affixed between the hub and the band, the rotor periphery being defined by the peripheral surface of the band with the gap being defined between the peripheral surface of the band and the casing.

3. A rotary pump for driving fluid, and the pump comprising:

a stationary casing, at least one rotor rotatably mounted in the casing, the rotor comprising a hub and at least one impelling blade in the hub, for impelling the fluid, a gap between a periphery of the rotor and the stationary casing, and at least one conduit in the rotor for conducting a by-passed portion of the fluid under pumping, the conduit having an outlet located at the periphery of the rotor and communicating with the gap, and an inlet located radially inwardly relative to the outlet, wherein the by-passed portion of fluid enters the inlet of the conduit and exists the outlet of the conduit into the gap to form a pressurized fluid seal between the rotor and the casing and a coaxial outer band having an outer axisymetrical peripheral surface, the blade being affixed between the hub and the band, the rotor periphery being defined by the peripheral surface of the band with the gap being defined between the peripheral surface of the band and the casing.

4. The scaling means of claim 3, wherein the casing defines an annular recess and the band is rotatably housed in the recess, with the gap being defined between the band the casing within the recess.

5. The sealing means of claim 3, wherein the hub includes a plurality of impelling blade, and each blade include at least one conduit radially outwardly extending through the blade.

6. The rotary pump of claim 3, wherein the at least one rotor comprises:

two adjacent rotors independent from each other and rotating in opposite directions.

* * * * *